US005482050A

United States Patent [19]
Smokoff et al.

[11] Patent Number: 5,482,050
[45] Date of Patent: Jan. 9, 1996

[54] METHOD AND SYSTEM FOR PROVIDING SAFE PATIENT MONITORING IN AN ELECTRONIC MEDICAL DEVICE WHILE SERVING AS A GENERAL-PURPOSE WINDOWED DISPLAY

[75] Inventors: Timothy L. Smokoff, Renton; Erik R. Horsley, Redmond, both of Wash.

[73] Assignee: SpaceLabs Medical, Inc., Redmond, Wash.

[21] Appl. No.: 198,100

[22] Filed: Feb. 17, 1994

[51] Int. Cl.$^6$ .................................................. G06F 159/00
[52] U.S. Cl. .................... 128/710; 128/660.04; 395/158; 395/159; 395/161; 395/650
[58] Field of Search .................... 364/413.01, 413.02, 364/413.03, 413.04, 413.05, 413.06, 413.07, 413.1, 413.11; 395/157, 158, 650, 140, 159, 161; 340/825.32, 825.5, 825.51; 345/133; 128/710, 712, 661.03, 660.04

[56] References Cited

U.S. PATENT DOCUMENTS

| | | | |
|---|---|---|---|
| 4,410,938 | 10/1983 | Higashiyama | 395/575 |
| 4,484,302 | 11/1984 | Cason et al. | 395/158 |
| 4,542,376 | 9/1985 | Bass et al. | 345/120 |
| 4,550,315 | 10/1985 | Bass et al. | 345/199 |
| 4,688,167 | 8/1987 | Agarwal | 395/650 |
| 4,710,767 | 12/1987 | Sciacero et al. | 345/191 |
| 4,794,386 | 12/1988 | Bedrij et al. | 345/119 |
| 4,899,136 | 2/1990 | Beard et al. | 345/156 |
| 4,954,818 | 9/1990 | Nakane et al. | 345/120 |
| 5,001,469 | 3/1991 | Pappas et al. | 345/120 |
| 5,062,060 | 10/1991 | Kolnick | 395/159 |
| 5,072,409 | 12/1991 | Bottorf et al. | 395/137 |

(List continued on next page.)

OTHER PUBLICATIONS

"Patient Monitor Human Interface Design"–Tivig, et al., Hewlett–Packard Journal vol. 42, Issue n.4, 11 pages, published Oct. 1991.

"The Integration of Text, Graphics, and Radiographic Images on X–Terminal Clinical Workstations"–London, et al. Medinfo '92, Elsevier Science Publishers, B.V. (North–Holland), published 1992, pp. 41–46.
Software Product: Chartcomp by Electronic Cottage Associates, in Datapro Software Catalog, record created Jan. 11, 1992 (Accession #00244614).
MacIntosh User's Guide, by Apple Computer, Inc., published 1992, pp. 98–99.
Cowart, Robert: *Mastering Windows 3.1*, published by Sybex, Inc, published 1992, p. 420.

*Primary Examiner*—David M. Huntley
*Assistant Examiner*—Joseph Thomas
*Attorney, Agent, or Firm*—Seed and Berry

[57] ABSTRACT

A method and system for providing safe patient monitoring in an electronic medical device while serving as a general-purpose windowed display is provided. In a preferred embodiment, an electronic medical device is capable of providing services to executing programs in response to requests for services from executing programs. These requests for services each specify a service to be provided. The electronic medical device ensures the integrity of an executing patient monitoring program while simultaneously providing services to a non-patient monitoring program that is executing. The electronic medical device provides the service specified by each request for services from the executing patient monitoring program and declines to provide services as they are specified by requests for services from the executing nonpatient monitoring program if provision of the service as specified would interfere with the executing patient monitoring program. In one embodiment, the electronic medical device omits to provide any service in response to a request for services from the executing nonpatient monitoring program that specifies a service that would interfere with the executing patient monitoring program. In one embodiment, the electronic medical device provides a service specified by the executing non-patient monitoring program in a manner different from that specified in the request for services, where the service provided in the different manner does not interfere with the executing patient monitoring program.

27 Claims, 5 Drawing Sheets

U.S. PATENT DOCUMENTS

| | | | |
|---|---|---|---|
| 5,128,658 | 7/1992 | Pappas et al. | 345/199 |
| 5,153,577 | 10/1992 | Mackey et al. | 345/149 |
| 5,179,655 | 1/1993 | Noguchi et al. | 395/158 |
| 5,185,858 | 2/1993 | Emery et al. | 395/158 |
| 5,220,312 | 6/1993 | Lumelsky et al. | 345/190 |
| 5,237,653 | 8/1993 | Noguchi et al. | 395/158 |
| 5,243,607 | 9/1993 | Masson et al. | 371/69.1 |

METHOD AND SYSTEM FOR PROVIDING SAFE PATIENT MONITORING IN AN ELECTRONIC MEDICAL DEVICE WHILE SERVING AS A GENERAL-PURPOSE WINDOWED DISPLAY

DESCRIPTION

1. Technical Field

The invention relates generally to a method and system for presenting visual output in an electronic medical device, and more specifically, to a method and system for providing safe patient monitoring while serving as a general-purpose windowed display.

2. Background of the Invention

Electronic medical devices such as electrocardiogram (E.C.G.) monitors are generally used to monitor a patient's condition using medical sensors and/or to deliver medical care via automatic medical care delivery systems. These devices have long been able to display information directly relating to patient condition or medical care delivery in both graphical and textual forms. For example, an E.C.G. monitor might display an electrocardiograph waveform and associated text, e.g., pulse rate. This information, displayed together, is called a physiological parameter.

These electronic medical devices have customarily employed custom hardware and software to achieve their results. The advent of general-purpose computing software, however, has made it expeditious to implement electronic medical devices using some general-purpose software. In fact, using general-purpose software permits the implemented electronic medical device to leverage existing operating systems, graphical operating environments, and application programs. The use of existing operating systems and graphical environments makes the implemented electronic medical device more flexible by providing a ready-made development environment in which third-party vendors may develop add-on software products that can execute on the electronic medical device.

In particular, it is desirable to permit third-party applications, such as a calculator application, to execute in a graphical operating environment, such as the public domain X-Window distributed operating environment, along with the monitoring programs that perform the primary monitoring function of the electronic medical device. This permits the third-party applications to display output in a window on the display device and receive input from input devices connected to the electronic medical device.

In many cases, however, third-party applications can interfere with the primary monitoring function of the electronic medical device. Third-party applications can, in many cases, capture all user input for extended periods of time, lockup the processor when a run-time error occurs, change the color of monitoring display, or obscure or generally disrupt the display organization. Such interference with the primary monitoring function of the electronic medical device is a matter of great concern, as it could cause important information from the electronic medical device to go unobserved by personnel monitoring the electronic medical device, adversely impacting patient care.

First, in most windowed operating environments, all the active applications are eligible to receive user input. User input in most windowed operating environments is directed to the application which has the input focus. Typically, the cursor is used to select the application window which is to have the input focus. In many window operating environments, however, a single application can "capture" the cursor and prevent the system and operator from changing the input focus. This permits third-party applications to deprive patient monitoring applications of user input for extended periods of time. This deprivation can significantly interfere with the primary monitoring functions of the electronic medical device such as acknowledging alarm events, turning alarms off, or just generally interacting with the electronic medical device.

In many windowing systems, capturing the cursor also causes the display contents to "freeze" until the cursor is "released." A typical example is scroll bars that update the display only after a user has positioned the scroll bar and released the cursor. Under this circumstance, however, stale or incorrect patient information will be displayed while the electronic medical device's display is frozen.

Second, in many windowed operating environments, when a runtime error occurs during the execution of a request from a third-party application, "processor lockup" occurs. This is a condition of a processor which prevents it from completing the execution of the current request and proceeding to execute further requests. If a third-party application causes processor lockup to occur, requests from patient monitoring applications waiting for execution cannot be executed. This interferes with the primary monitoring function of the electronic medical device by preventing the display of important patient monitoring information.

Third, most windowed operating environments permit third-party applications to modify the colors used to display information. Most graphical operating environments maintain a single color table to map virtual colors, understood by applications, to actual color values that may be displayed on a display device. In order to be able to select the actual colors displayed, each application is permitted to change the contents of the color table. The number of colors required by all the applications often exceeds the capacity of the color table. When this occurs, most windowed operating environments permit applications to maintain their own virtual color map, which is loaded into the physical color map whenever that particular application has the input focus. This has the side effect of changing the display colors for the entire display adversely affecting the rest of the applications. For instance, a third-party application could change the actual color of the monitoring applications information to the actual color of the background making the patient information invisible. This would also allow third party applications to change monitoring applications colors which have special significance, e.g., red for an alarm condition, to another color having a different significance, e.g., blue for a non-alarm condition. In this example, an alarm condition could be displayed in blue instead of red, giving those monitoring the electronic medical device the false impression that no alarm condition is active.

Fourth, most modern windowing environments support overlapping windows in which windows are permitted to overlay some or all of the area of other windows. This permits a third-party application's window to overlay important information displayed by the monitoring applications. For example, a user of a third-party application may drag the window containing output from the third-party application to a portion of the display occupied by important information such as alarm notification messages. At this point, the important information "displayed" by the monitoring programs is actually obscured by the applications window, and cannot be seen by those monitoring the electronic medical device. Important command windows or notifications of alarm events needed by the user to begin monitoring new conditions or otherwise control the state of the electronic medical device can likewise be overlaid.

Fifth, because users can rearrange the contents of the display as described above, the display may be left in completely different states. For example, windows for various third-party applications may be scattered about the display area. Portions of the information displayed by the monitoring programs may be relocated and obscured, as may be command windows. This makes it confusing for a different user, or even the same user returning later, to locate important information or command windows.

Because user interface reliability problems in electronic medical devices could compromise the health, or even life of the patients on which they are used, it is especially important that they be addressed in any system that supports the use of third-party applications in a windowed operating environment.

SUMMARY OF THE INVENTION

It is an object of the invention to provide, in an electronic medical device capable of providing services to executing programs in response to requests for services from executing programs, the requests for services specifying a service to be provided, a method and system for ensuring the integrity of an executing patient monitoring program.

It is another object of the invention to provide, in an electronic medical device having both a microprocessor and a display device, the display device having a display area, a method and system for ensuring the integrity of the display of the output of patient monitoring programs while simultaneously displaying the output of additional executing programs.

These and other objects, which will become apparent as the invention is more fully described below, are provided by a method and system for providing safe patient monitoring in an electronic medical device while serving as a general-purpose windowed display. In a preferred embodiment, an electronic medical device is capable of providing services to executing programs in response to requests for services from executing programs. These requests for services each specify a service to be provided. The electronic medical device ensures the integrity of an executing patient monitoring program while simultaneously providing services to an executing non-patient monitoring program. The electronic medical device provides the service specified by each request for services from the executing patient monitoring program and declines to provide services as they are specified by requests for services from the executing non-patient monitoring program if provision of the service as specified would interfere with the executing patient monitoring program. In one embodiment, the electronic medical device refuses to provide any service in response to a request for services from the executing non-patient monitoring program that specifies a service that would interfere with the executing patient monitoring program. In one embodiment, the electronic medical device provides a service specified by the executing non-patient monitoring program in a manner different from that specified in the request for services, where the service provided in the different manner does not interfere with the executing patient monitoring program.

DETAILED DESCRIPTION OF THE INVENTION

I. Overview

The inventive method and system provides safe patient monitoring in an electronic medical device while serving as a general-purpose windowed display. In a preferred embodiment, system services are provided in the electronic medical device that protect the integrity of the primary monitoring function of the electronic medical device from interference caused by third-party application programs (third-party applications). These system services, along with specialized hardware, intervene to prevent extended user input capture, detect and correct run-time processor lockup, provide separate color tables for monitoring programs and third-party applications, enforce protected regions within the display area into which output from the third-party applications cannot be moved, provide a command that is always available to users for returning the display area to a standard organization, optionally restrict the number of visible third-party applications, and iconify large third-party application windows when a monitoring alarm condition occurs. In a preferred embodiment, the system services described are provided by modifying aspects of the standard version of X-Windows, a public domain distributed operating environment and by fabricating specialized hardware for executing the operating environment and other programs.

Figure 1:
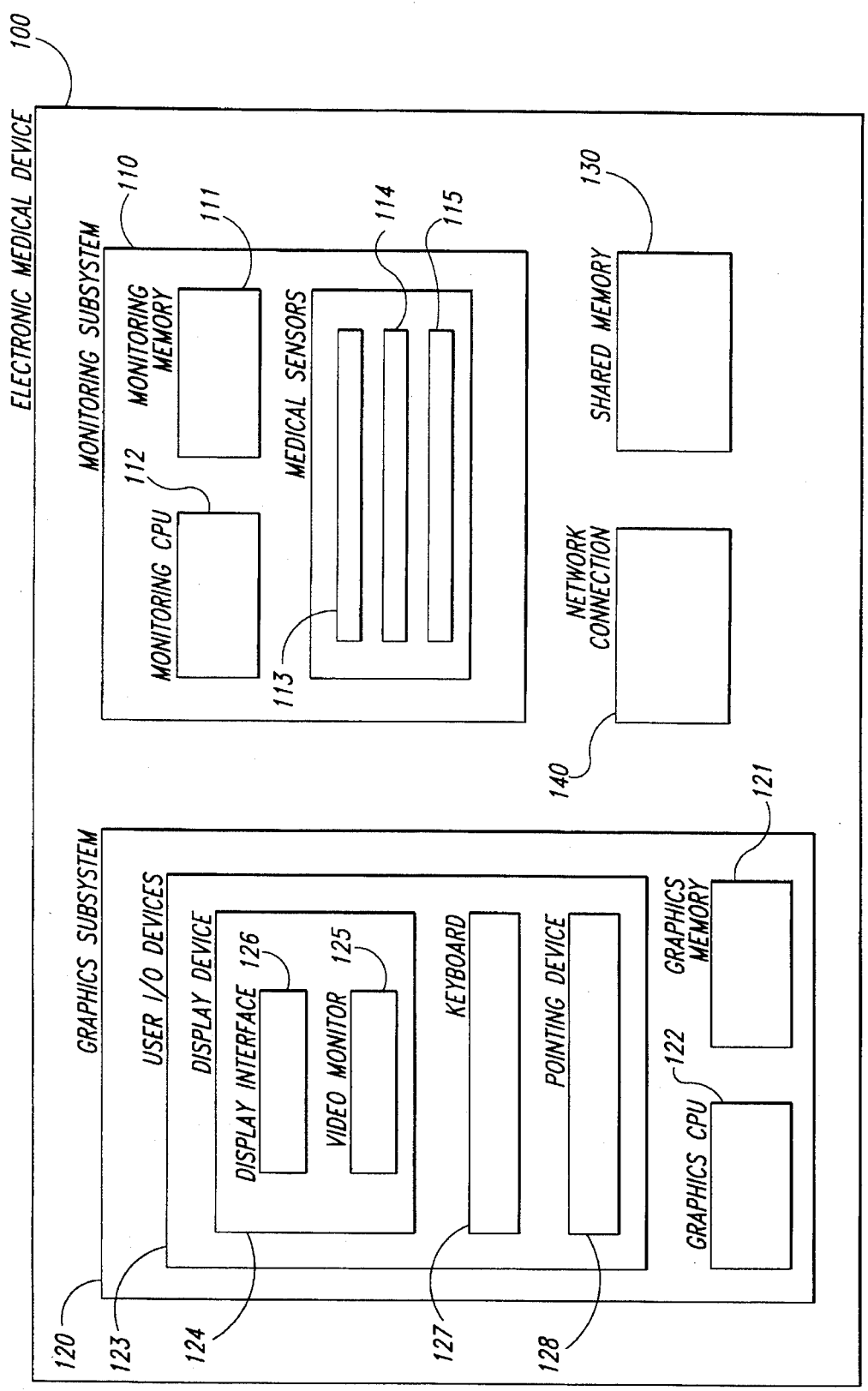
FIG. 1 is a high-level block diagram of the electronic medical device in which a preferred embodiment of the invention operates.

FIG. 1 is a high-level block diagram of the electronic medical device in which a preferred embodiment of the invention operates. The electronic medical device 100 contains a patient monitoring subsystem (monitoring subsystem) 110 for collecting and analyzing patient data and a graphics subsystem 120 for displaying output and receiving user input for both patient monitoring applications and non-patient monitoring applications. The electronic medical device also includes shared memory 130 that may be accessed by both the monitoring subsystem and the graphics subsystem. The electronic medical device further includes a network connection 140 that may be used by both the monitoring subsystem and the graphics subsystem to communicate with other computer systems connected to the electronic medical device by a network. The monitoring subsystem contains dedicated monitoring memory (monitoring memory) 111, a monitoring central processing unit (monitoring CPU) 112 and medical sensors 113–115, such as E.C.G. electrodes or pulse oximetry sensors, to monitor patients. Patient data from the medical sensors is stored in the monitoring memory and analyzed by the monitoring CPU. The monitoring CPU requests display services from the graphics subsystem in order to display the results of patient data analysis. The graphics subsystem supports user input/output devices 123 with which to display information, including messages, to users and accept input from them. Among the user input/output devices is a display device 124 comprising a video monitor 125, for displaying information, and a display interface 126 for controlling and transmitting information to the video monitor. The user input/output devices further include a keyboard 127 and a pointing device 128, such as a mouse. The programs required to provide the system services of the preferred embodiment, as well as monitoring programs and third-party applications, reside in the graphics memory. The graphics memory is preferably a solid-state memory device whose contents may be permanent or may be loaded from, a local disk drive or a remote disk drive controlled by a separate computer system to which the electronic medical device 100 is connected via the network connection. The above programs execute on a graphics CPU 122, or on the CPU of a separate computer system to which the electronic medical device 100 is connected via the network connection.

II. Prevent Extended User Input Capture

When a third-party application captures the cursor, all subsequent user input is directed to the capturing third-party application. While this is necessary in some situations, e.g., to cause a scroll bar in the third-party application's window to function properly, the longer the capture continues, the longer the patient monitoring programs are deprived of any user input and the display contents are frozen. Since this can prevent users from performing necessary interaction with patient monitoring programs and cause stale or incorrect information to be displayed, the electronic medical device limits the amount of time for which any third-party application can capture the focus. The electronic medical device preferably starts a countdown each time a third-party application captures the cursor. If a preselected period of time elapses before the capturing third-party application releases the cursor, the electronic medical device forces the capturing third-party application to release the cursor allowing the display to be refreshed and the input focus changed.

III. Detect and Correct Run-Time Processor Lockup

Run-time errors encountered by the electronic medical device's graphics processor while executing a request for a third-party application can cause the lockup of the graphics processor. This is a condition of a processor that prevents it from completing the execution of the current request and proceeding to execute further requests. To detect and correct run-time processor lockup, a graphics processor lockup watchdog is preferably included in the electronic medical device. The graphics processor lockup watchdog (watchdog) is a hardware-implemented countdown timer that counts down from a preselected interval and, when the interval expires, concludes that graphics processor lockup has occurred and attempts to correct it. The graphics processor, when it is operating normally, repeatedly refreshes the watchdog before enough time elapses for the interval to expire, restarting the interval. When the graphics processor encounters a run-time error causing a loadup, the graphics processor is unable to refresh the watchdog. The interval then expires, and the watchdog blanks the display area to prevent the display of old or incorrect information stored in display memory. The watchdog then signals the monitoring processor to attempt to correct the graphics processor lockup by raising a monitoring processor interrupt. The monitoring processor, in response to the interrupt, attempts to correct the graphics processor lockup by first canceling the request that the graphics processor is currently executing. If this fails, the monitoring processor attempts to correct the graphics processor lockup by resetting the graphics processor. If this fails, the monitoring processor attempts to correct the graphics processor lockup by warmstarting the electronic medical device, clearing the contents of graphics subsystem memory and shared memory, but maintaining the contents of monitoring subsystem memory which contains patient information.

IV. Provide Separate Color Tables

Generally, all applications display information on the display device by selecting a real color value (typically 24 bits) in which the information should be displayed, storing a mapping in a central color mapping table that maps to the selected real color value from some virtual color value small enough to fit in the storage allocated for each pixel in display memory (typically 8 bits), and using drawing routines to change the value of the display memory locations corresponding to the desired pixels to the virtual color value used in the mapping. When the display interface periodically refreshes the displayed contents of the video monitor, it reads the virtual colors from display memory, maps them to real color values using the mapping table, transforms the digital real color value into an analog real color signal using one or more digital-to-analog converters, and refreshes the video monitor with the analog signal.

When a third-party application has the focus, it can change mappings stored in the color mapping table. Any mappings stored earlier by the monitoring programs in the color mapping table would therefore usually be subject to undesirable modification by third-party applications. In order to prevent this, one or more additional color mapping tables are allocated within the display interface and an attribute portion containing one or more mapping table selection bits is preferably added to the data portion of each pixel in display memory. The mapping table selection bits are used by the display interface to determine which color table to use to display a given pixel. The Window Manager, which is responsible for initializing pixels to display newly opened windows, is preferably modified to also initialize the color table mapping bits. When a third-party application opens a window, the Window Manager sets the color table mapping bits for each pixel in the window to designate a default color mapping table. This is the color mapping table that is modified when the standard X-Windows service for modifying the color mapping table is invoked. The other color mapping tables are reserved for use by the monitoring applications. When a monitoring program opens a window, the Window Manager sets the color table mapping bits for each pixel in the window to designate one of the additional color mapping tables. Because the monitoring programs are aware of the additional color mapping tables, they are able to invoke a special service, unknown to third-party applications, to modify the additional color mapping tables. When the display interface sees the color table selection bits that designate one of the additional color mapping tables when displaying pixels displayed by a monitoring program, it uses the appropriate color mapping table to map the virtual color value to an actual color value. Because the monitoring programs are unaware of the additional color mapping tables, they cannot modify the mappings stored therein by monitoring programs, and may therefore not alter the actual colors in which the monitoring programs display information.

In a preferred embodiment, two phantom memory regions are created in memory that both resolve to the actual display memory. The first of these phantom memory ranges is supplied to programs for passing to drawing routines called to display information. This range maps to the data portion of each pixel in display memory, where the virtual color value is stored. When programs use drawing routines to modify the first phantom memory region, they modify only the data portions of display memory containing only virtual color values, and do not affect the attribute portions of display memory containing color map selection bits. The second of these phantom memory ranges is used to set attributes for each pixel stored in the attribute portions of the representation of each pixel in display memory. Attributes include color mapping table selection bits, as well as other data required to administer the display for monitoring programs. This other data includes indications of whether the pixel will be used to display patient physiological parameters or real-time video, each using custom drawing facilities instead of the standard X-Windows drawing routines. The other data also includes indications of whether the other bits of the attribute portion and all of the bits of the data portion together contain a truncated real color value, called a true color value, to be displayed by the display interface without color mapping. The second phantom range is used by the modified window manager to quickly initialize or change the attributes for a group of pixels without changing the virtual color value of any of pixels in the group.

V. Enforce Protected Regions

In the preferred embodiment, protected regions include critical patient information such as high priority physiological parameters and a patient status area used to notify the operator of local alarm events. Command windows are also protected. The command windows are made up of menu keys that are used by the operator to invoke commands that modify the state of the electronic medical device such as acknowledging alarm events. The window manager monitors window open and movement requests made by the applications to the X-Window X-Server. When the Window Manager observes a request from an application window to overlap a protected region, the Window Manager submits a request to the X-Server to move the window to a new, nearby location outside of all the protected zones. This prevents any application from overlapping the contents of a protected region.

Figure 2A:
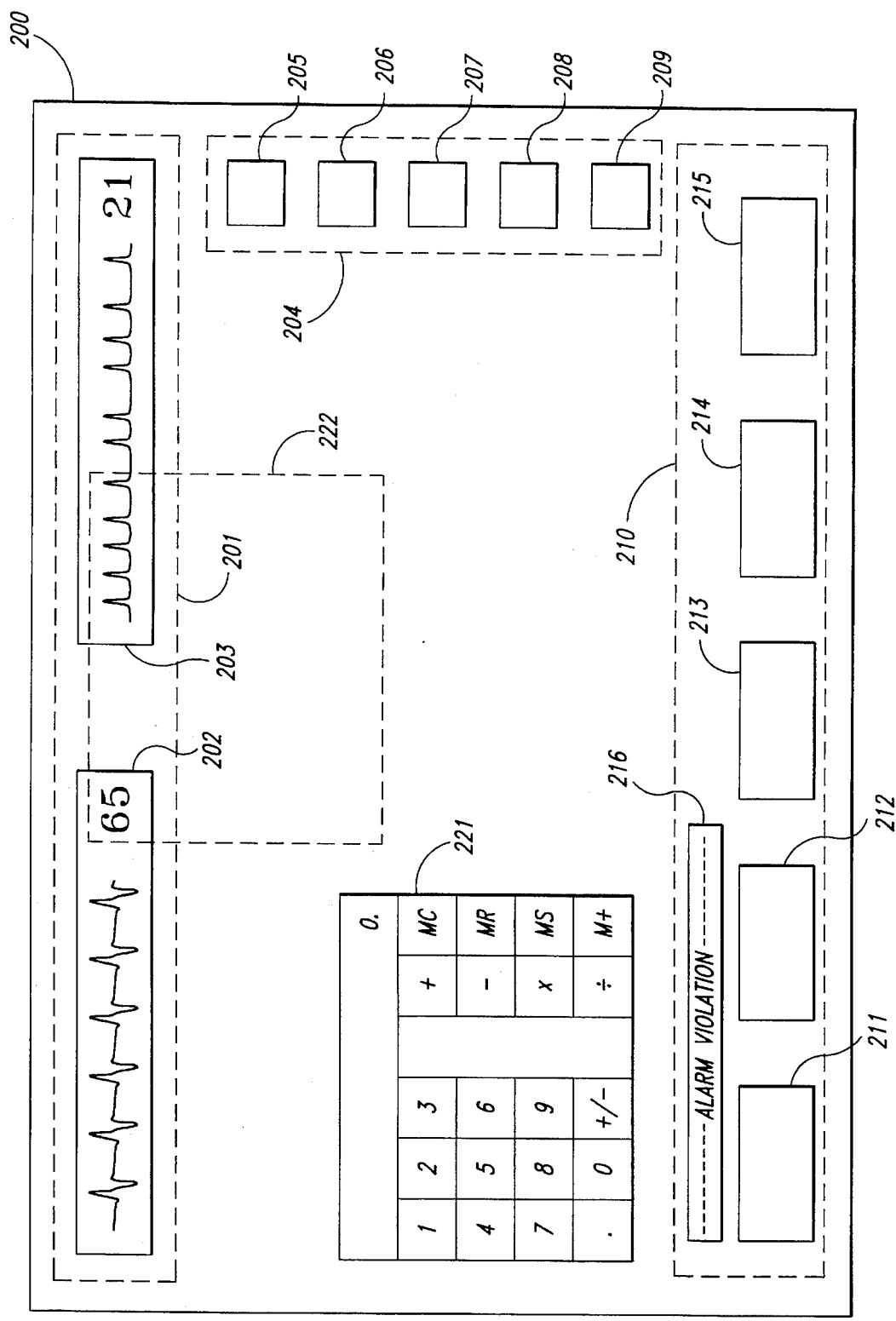
FIGS. 2A–2B are display images showing an example of protected regions enforcement.
Figure 2B:
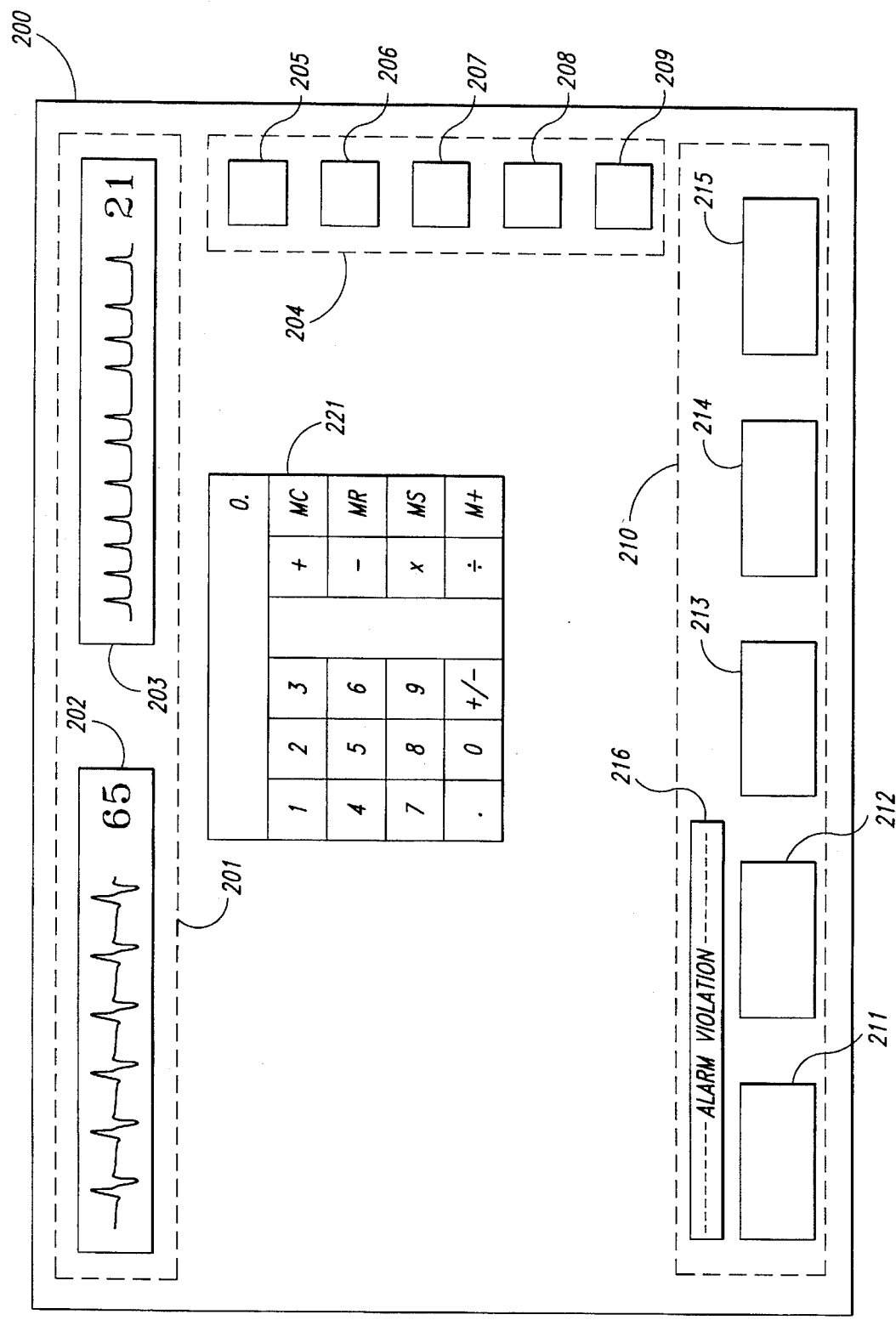

FIGS. 2A–2B are display images showing an example of protected regions enforcement. The display area 200 contains protected regions 201, containing important patient parameters 202 and 203; 204, containing hard keys 205–209; and 210, containing soft keys 211–215 and patient status area 216. A user uses a pointing device to move the window for a third-party calculator program 22 1 in its present location to a target location shown in FIG. 2A by a broken-line box 222. The target location overlays a protected region 201 encompassing important patient parameters 202 and 203. The third-party application program submits a request to the X-Server to move the window to the new location. The Window Manager observes the request, determines that the target location is within a protected region, and submits an instruction to the X-Server to move the window to location 221, outside of all of the protected regions as shown in FIG. 2B.

An application may request that the Window Manager display its output window in a full-screen mode. In this mode, the entire display is used to display the requesting application's window. In a preferred embodiment, the electronic medical device relaxes protected region enforcement when an application requests the full-screen display of its window to permit the satisfaction of the request. That is, the electronic medical device satisfies full-screen requests, even though they encroach on all of the protected regions. In order to ensure that the satisfaction of a request for full-screen mode does not obscure alarm condition messages, the Window Manager is preferably modified to iconify any full-screen window as soon as the electronic medical device encounters an alarm condition. This permits the electronic medical device to display the alarm condition message without it being obscured by the full-screen window. The Window Manager is further preferably able to iconify any window larger than a configurable threshold area when the electronic medical device encounters an alarm condition, making it less likely that alarm condition messages will be obscured by any display window.

VI. Provide Command For Returning The Display Area To A Standard Organization

A "normal screen" command for returning the display area to a standard organization is preferably always available to the user. A command window, preferably a hard key as described above, is displayed in a protected region, permitting the user to invoke the normal screen command at any time. The command window may be invoked by a user when the contents of the display area have become rearranged and confusing to return the display area to a familiar organization in which important information can be readily located.

Figure 3A:
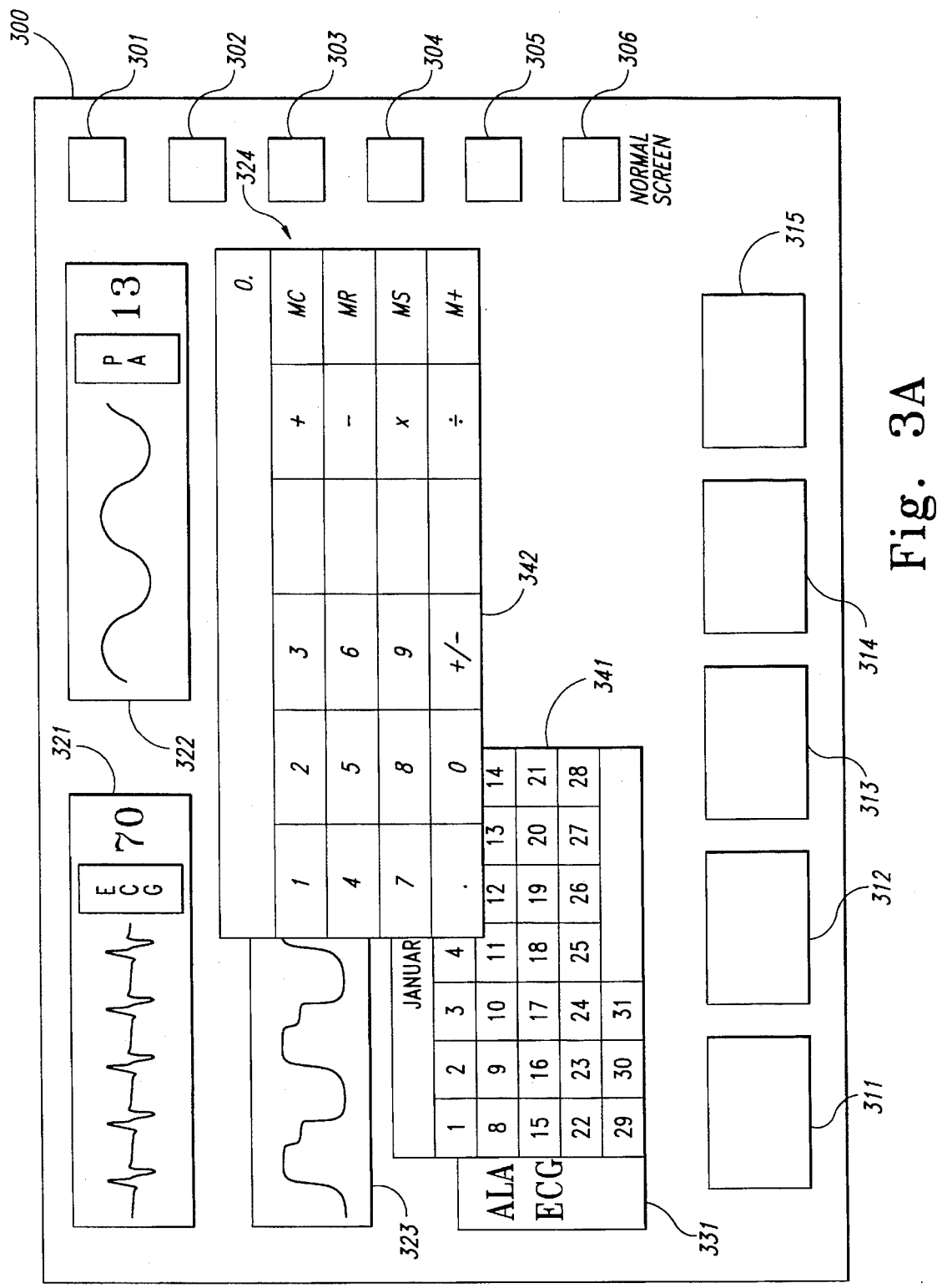
FIGS. 3A–3B are screen images showing the operation of the normal screen command window.
Figure 3B:
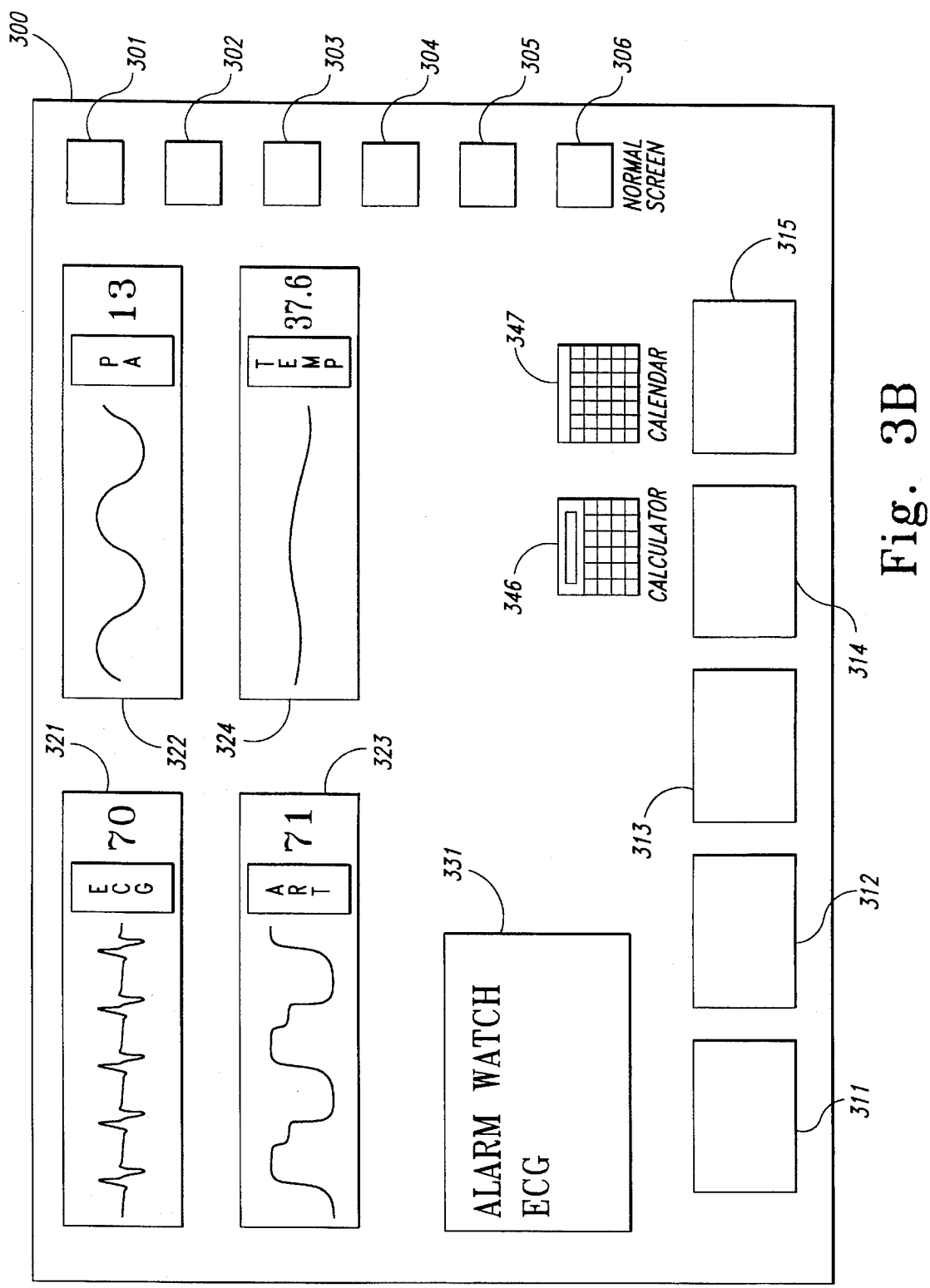

FIGS. 3A–3B are screen images showing the operation of the normal screen command window. FIG. 3A shows the contents of the display area 300 in a relatively confusing state. The display area contains hard keys 301–306, including "normal screen" hard key 306, soft keys 311–315. High priority patient parameters 321 and 322 are completely visible, but other patient parameters are not: patient parameters 323 is partially obscured by a calendar application window 341, and patient parameter 324 is completely obscured by a calculator application window 342. An alarm watch window 331 is also partially obscured by a calendar application window 341. In order to return the display area to a familiar organization in which important information can be readily located, the user uses the pointing device to activate the normal screen hard key.

In response to the activation of the normal screen hard key, the electronic medical device returns the display to a standard organization. The electronic medical device "iconifies" any application programs, or closes their windows and displays small icons in their place. This leaves only patient and alarm watch windows visible. The user may restore the window for any iconified application in its original location by using the pointing device to select its icon. This is shown in FIG. 3B. The calendar application window 341 and calculator application window 342 have been iconified, replaced with calendar icon 347 and calculator icon 346, respectively. This has the effect of making patient parameters 323 and 324 as well as alarm watch window 33 1, completely visible.

VII. Optionally Restrict The Number Of Visible Third-Party Applications

The user is permitted to specify a special display mode in which only a predetermined maximum number of third-party application are visible at a given time. In view of the low tolerance of beginner users for display complexity, the maximum number is preferably one. This restriction is implemented by modifying the Window Manager to keep track of the number of third-party applications that have open windows. If the Window Manager receives a request from a third-party application to open a new window, and if the user has specified the special display mode, and if the number of third-party applications that have open windows is equal to the maximum number of third-party applications, then the Window Manager selects a third-party application having an open window to iconify. The Window Manager preferably selects the third-party application with an open window that has the lowest priority. The Window Manager then iconifies the selected third-party application so that its window is no longer displayed and continues to open a new window in response to the request. This limits the extent to which important monitoring information can be obscured from the user.

VIII. Conclusion

While this invention has been shown and described with reference to preferred embodiments, it will be understood by those skilled in the art that various changes or modifications in form and detail may be made without departing from the scope of the invention. For example, virtually each aspect of the invention could be implemented either in software or hardware design.

We claim:

1. In an electronic medical device capable of providing services to executing programs in response to requests for services from executing programs, the requests for services specifying a service to be provided, a method for ensuring the integrity of an executing patient monitoring program while simultaneously providing services to an executing non-patient monitoring program, the method comprising the steps of:

executing the patient monitoring program;

providing the service specified by each request for services from the executing patient monitoring program;

executing the non-patient monitoring program; and declining to provide services as specified by requests for services from the executing non-patient monitoring program if provision of the service as specified would interfere with the executing patient monitoring program, wherein at least a portion of the requests for services from executing programs specify a window display service for displaying a window containing output from the requesting application, the displayed window having an area, and wherein, for these requests, the declining step is accomplished by the steps of:

providing the window display service specified by the executing non-patient monitoring program;

detecting an alarm condition; and upon detecting the alarm condition, if the displayed window has an area greater than a threshold area, reducing the area of the displayed window.

2. The method of claim 1 wherein the step of declining to provide services is accomplished by omitting to provide any service in response to a request for services from the executing non-patient monitoring program that specifies a service that would interfere with the executing patient monitoring program.

3. The method of claim 2 wherein the electronic medical device has a display device having a display area, and wherein at least a portion of the requests for services from executing programs specify a display service for displaying specified output within the display area, and wherein the providing step is accomplished by displaying the output specified by the request in a location within the display area that is substantially the same as the location specified by the request, and wherein the step of omitting to provide any service that would interfere with the executing patient monitoring program by omitting to display the output specified by the request if the display of the output specified by the request would interfere with the display of output by the executing patient monitoring program.

4. The method of claim 2 wherein the electronic medical device maintains a patient monitoring program color mapping table for mapping virtual color values used by the executing patient monitoring program to real color values, and wherein at least a portion of the requests for services from executing programs specify a patient monitoring program color mapping table alteration service for altering the real color value to which a specified virtual color value used by the executing patient monitoring program maps in the patient monitoring program color mapping table, and wherein the providing step responds to requests specifying the patient monitoring program color mapping table alteration service from the executing patient monitoring program by altering the real color value to which a specified virtual color value used by the executing patient monitoring program maps in the patient monitoring program color mapping table, and wherein the step of omitting to provide any service that would interfere with the executing patient monitoring program is accomplished by responding to requests specifying the patient monitoring program color mapping table alteration service from the executing non-patient monitoring program by omitting to alter the real color value to which the specified virtual color value used by the executing patient monitoring program maps in the patient monitoring program color mapping table.

5. The method of claim 1 wherein requests for services from executing programs further specify, a manner in which the services to be provided, and wherein the step of declining to provide services is accomplished by adaptively providing a service specified by the executing non-patient monitoring program in a manner different from that specified in the request for services that does not interfere with the executing patient monitoring program.

6. The method of claim 5 wherein the electronic medical device has a display device having a display area, and wherein at least a portion of the requests for services from executing programs specify a display service for displaying specified output at a specified location within the display area, and wherein the providing step is accomplished by displaying the output specified by the request in a location within the display area that is substantially the same as the location specified by the request, and wherein the adaptively providing step is accomplished by displaying the output specified by the request in a location within the display area that is as close to the location specified by the request as is possible without interfering with the display of output by the executing patient monitoring program.

7. The method of claim 5 wherein the electronic medical device maintains a patient monitoring program color mapping table for mapping virtual color values used by the executing patient monitoring program to real color values, and wherein at least a portion of the requests for services from executing programs specify a patient monitoring program color mapping table alteration service for altering the real color value to which a specified virtual color value used by the executing patient monitoring program maps in the patient monitoring program color mapping table, and wherein the electronic medical device also maintains a non-patient monitoring program color table for mapping virtual color values used by the executing non-patient monitoring program to real color values, and wherein the providing step responds to requests specifying the patient monitoring program color mapping table alteration service from the executing patient monitoring program by altering the real color value to which a specified virtual color value used by the executing patient monitoring program maps in the patient monitoring program color mapping table, and wherein the adaptively providing step is accomplished by responding to requests specifying the patient monitoring program color mapping table alteration service from the executing non-patient monitoring program by altering the real color value to which a specified virtual color value used by the executing non-patient monitoring program maps in the non-patient monitoring program color mapping table.

8. The method of claim 5 wherein at least a portion of the requests for services from executing programs specify a user input capture service for capturing substantially all of the input provided by a user, and wherein requests for services that specify the user input capture service also specify a user input capture duration, and wherein the providing step is accomplished by providing the user input capture service for the specified user input capture duration, and wherein the adaptively providing step is accomplished by providing the user input capture service for a duration not exceeding a predetermined maximum duration.

9. The method of claim 5 wherein the adaptively providing step is accomplished by the steps of:

providing the service specified by the executing non-patient monitoring program;

detecting a run-time error during the provision of the service; and upon detecting the run-time error, ceasing to provide the service specified by the executing non-patient monitoring program.

10. The method of claim 9 wherein the ceasing to provide step is accomplished by resetting the electronic medical device.

11. The method of claim 1 wherein the step of reducing the area of the displayed window includes the step of iconifying the displayed window.

12. In an electronic medical device having a microprocessor, a display device, and an input device, the display device having a display area, a method for ensuring the integrity of the display of the output of patient monitoring programs while simultaneously displaying the output of additional executing programs, the additional programs being capable of capturing input from the input device, the method comprising the steps of:

limiting the duration of input capture by any of the additional programs;

using an additional program display color mapping table that is modifiable by the additional programs to display the output of the additional programs and a separate patient monitoring program display color mapping table that is modifiable by the patient monitoring programs and unmodifiable by the additional programs to display the output of the patient monitoring programs;

preventing the display of the output of the additional programs in predefined protected regions within the display area;

in response to receiving a normal screen command, redisplaying the contents of the display area in a preselected standard organization;

in response to a request from the executing additional program, displaying a window for containing output or the executing additional program;

detecting an alarm condition; and upon deleting the alarm condition, if the displayed window has an area greater than a threshold area reducing the area of the displayed window.

13. The method of claim 12, further including the steps of:

detecting a run-time error while displaying the output of an executing program; and clearing the detected run-time error.

14. The method of claim 12, further including the step of limiting the number of additional programs that may display information in the display area to a predetermined maximum number of additional programs.

15. The method of claim 14 wherein the limiting step includes the steps of:

in response to a request to display the output of one of the additional programs, comparing the number of the additional programs presently executing to the predetermined maximum number of the additional programs;

approving the request to display the output of one of the additional programs; and if the number of the additional programs presently executing is not less than the predetermined maximum number of additional programs, iconifying the output displayed in accordance with an earlier-approved request to display the output of one of the additional programs.

16. The method of claim 12 wherein the display area is comprised of pixels, each of the pixels being periodically refreshed with a real color value, and wherein the step of using separate display color mapping tables to display the output of the patient monitoring programs and the output of the additional programs includes steps of:

when a pixel in the display area to be refreshed, reading an attribute portion of the pixel representation corresponding to the pixel that is to be refreshed;

selecting one of a plurality of available color mapping tables based upon the read attribute portion of a virtual color value, each of the available color mapping tables mapping a virtual color value to a real color value;

reading a virtual color value portion of the pixel representation containing a virtual color value;

using the selected color mapping table to map the virtual color value of the read virtual color value portion of the pixel representation to a real color value; and refreshing the pixel using the real color value.

17. The method of claim 12 wherein the step of preventing the display of the output of the additional programs in predefined protected regions within the display area includes the steps of:

receiving a display request to display specified output of one of the additional programs in a specified target region within the display;

determining whether the specified target region of the received request intersects a protected region;

if the specified target region of the received request intersects a protected region:

identifying an alternate target region within the display that is near the specified target region and that does not intersect any protected region, and causing the specified output to be displayed in the alternate target region; and if the specified target region of the received request intersects no protected regions, causing the specified output to be displayed in the specified target region.

18. In an electronic medical device having both a microprocessor and a display device, the display device having a display area, a method for ensuring the integrity of the display of the output of patient monitoring programs while simultaneously displaying the output of additional executing programs by limiting the number of the additional programs that may display information in the display area to a predetermined maximum number of additional programs, the method comprising the steps of:

in response to a request to display the output of one of the additional programs, comparing the number of the additional programs presently executing to the predetermined maximum number of additional programs;

approving the request to display the output of one of the additional programs;

if the number of the additional programs presently executing is not less than the predetermined maximum number of additional programs, iconifying the output displayed in accordance with an earlier-approved request to display the output of one of the additional programs;

in response to the approving step, displaying the additional program output in a section of the display area:

detecting an alarm condition; and upon detecting the alarm condition reducing the area of the section of the display area in which the additional program output is displayed.

19. In an electronic medical device upon which programs may execute, the display device having a display area, a method for ensuring the integrity of the display of the output of patient monitoring programs while simultaneously displaying the output of additional executing programs by preventing the display of the output of the additional programs in predefined protected regions within the display area, the method comprising the steps of:

receiving a display request to display specified output of one of the additional programs in a specified target region within the display;

determining whether the specified target region of the received request intersects a protected region;

if the specified target region of the received request intersects a protected region:

identifying an alternate target region within the display that is near the specified target region and that does not intersect any protected region, and causing the specified output to be displayed in the alternate target region;

if the specified target region of the received request intersects no protected regions, causing the specified output to be displayed in the specified target region;

detecting an alarm condition; and upon detecting the alarm condition, if the displayed specified output has an area greater than a threshold area, reducing the area of the displayed specified output.

20. An electronic medical device capable of executing and displaying output for both patient monitoring programs and additional programs, the electronic medical device comprising:

a display device having a display area in which output for both patient monitoring programs and additional programs is displayed;

a memory for storing the patient monitoring programs and the additional programs;

a processor for executing the patient monitoring programs arid the additional programs;

a display interface for displaying visual output in the display area of the display device that uses an additional program display color mapping table that is modifiable by the additional programs to display the output of the additional programs and a separate monitoring program display color mapping table that is modifiable by the patient monitoring programs and unmodifiable by the additional programs to display the output of the patient monitoring programs;

a display regulator for preventing the display of the output of the additional programs in predefined protected regions within the display area;

a screen reorganizer for redisplaying the contents of the display area in a preselected standard organization in response to receiving a normal screen command; and an alarm condition message protector for reducing the size of windows displayed on the display device in response to the display of an alarm condition message on the display device in order to ensure the visibility of the alarm condition message.

21. The electronic medical device of claim 20, further including:

an input device from which input is received; and an input capture limiter for limiting the duration of any capture of input from the input device by an additional program.

22. The electronic medical device of claim 20, further including a processor watchdog for detecting and correcting the lockup of the processor.

23. The electronic medical device of claim 20 wherein the display regulator includes an additional program display limiter for limiting the number of additional programs that may simultaneously display output within the display area.

24. An electronic medical device capable of displaying output for both patient monitoring programs and additional programs, the electronic medical device comprising:

a display device having a display area in which output for both patient monitoring programs and additional programs is displayed;

a network connection for connecting via a network to a remote computer system for storing and executing the patient monitoring programs and the additional programs;

a display interface for displaying visual output in the display area of the display device that uses an additional program display color mapping table that is modifiable by the additional programs to display the output of the additional programs and a separate patient monitoring program display color mapping table that is modifiable by the patient monitoring programs and unmodifiable by the additional programs to display the output of the patient monitoring programs;

a processor regulator for inhibiting the monopolization of program execution resources of the remote computer system by any of the additional programs;

a display regulator for preventing the display of the output of the additional programs in predefined protected regions within the display area;

a screen reorganizer for redisplaying the contents of the display area in a preselected standard organization in response to receiving a normal screen command; and an alarm condition message protector for reducing the size of windows displayed on the display device in response to the display of an alarm condition message on the play device in order to ensure the visibility of the alarm condition message.

25. In an electronic medical device, a method for ensuring the integrity of an executing patient monitoring program while simultaneously providing services to an executing non-patient monitoring program, the method comprising the steps of:

in response to a request from the executing non-patient monitoring program, displaying a window for containing output of the executing non-patient monitoring program;

detecting an alarm condition; and upon detecting the alarm condition, if the displayed window has an area greater than a threshold area, reducing the area of the displayed window.

26. The method of claim 25 wherein the step of reducing the area of the displayed window includes the step of iconifying the displayed window.

27. An electronic medical device capable of executing and displaying output for both patient monitoring programs and additional programs, the electronic medical device comprising:

a display device having a display area in which output for both patient monitoring programs and additional programs is displayed;

a memory for storing the patient monitoring programs and the additional programs;

a processor for executing the patient monitoring programs and the additional programs; and an alarm condition message protector for reducing the size of windows displayed on the display device in response to the display of an alarm condition message on the display device in order to ensure the visibility of the alarm condition message.

\* \* \* \* \*

UNITED STATES PATENT AND TRADEMARK OFFICE
CERTIFICATE OF CORRECTION

PATENT NO. : 5,482,050
DATED : January 9, 1996
INVENTOR(S) : Timothy L. Smokoff and Erik R. Horsley It is certified that error appears in the above-identified patent and that said Letters Patent is hereby corrected as shown below:

In Column 11, Claim 12, Line 53, following "output", please delete "or" and insert therefor--of--.

In Column 11, Claim 12, Line 57, following "threshold area", please insert--,--.

In Column 13, Claim 18, Line 9, following "area", please delete ":'" and insert therefor--;--.

In Column 13, Claim 18, Line 11, following "condition", please insert--,--.

In Column 13, Claim 20, Line 55, please delete "arid" and insert therefor--and--.

In Column 14, Claim 24, Line 53, please delete "play" and insert therefor--display--.

Signed and Sealed this

Seventeenth Day of February, 1998

*Attest:*

BRUCE LEHMAN

*Attesting Officer*  *Commissioner of Patents and Trademarks*